United States Patent
Lundström et al.

(10) Patent No.: US 6,569,779 B1
(45) Date of Patent: May 27, 2003

(54) DEVICE FOR GAS SENSING

(75) Inventors: Ingemar Lundström, Linköping (SE); Per Mårtensson, Linköping (SE)

(73) Assignee: Nordic Sensor Technologies AB (SE)

( * ) Notice: Subject to any disclaimer, the term of this patent is extended or adjusted under 35 U.S.C. 154(b) by 0 days.

(21) Appl. No.: 09/674,871

(22) PCT Filed: May 6, 1999

(86) PCT No.: PCT/SE99/00760
§ 371 (c)(1),
(2), (4) Date: Jan. 8, 2001

(87) PCT Pub. No.: WO99/58964
PCT Pub. Date: Nov. 18, 1999

(30) Foreign Application Priority Data

May 8, 1998 (SE) .............................................. 9801610

(51) Int. Cl.$^7$ ............................................ H01L 21/302
(52) U.S. Cl. ....................................... 438/745; 438/619
(58) Field of Search .................. 438/482, 166, 438/785, 619, 245; 257/295; 333/186; 437/210; 73/504.13

(56) References Cited

U.S. PATENT DOCUMENTS

| | | | |
|---|---|---|---|
| 2,857,251 A | 10/1958 | Krogh | 23/232 |
| 3,595,621 A | 7/1971 | Andreatch | 23/254 E |
| 4,169,126 A | 9/1979 | Iles | 422/95 |
| 4,321,322 A | 3/1982 | Ahnell | 435/34 |
| 4,584,867 A | 4/1986 | Forster | 73/23 |
| 4,885,929 A | 12/1989 | Kasahara et al. | 73/23 |
| 4,897,162 A | 1/1990 | Lewandowski et al. | 204/1 T |
| 4,992,384 A | 2/1991 | Laurs et al. | 436/151 |
| 5,332,681 A | 7/1994 | Tonucci et al. | 437/16 |
| 5,545,377 A | 8/1996 | Fukaya et al. | 422/108 |
| 5,643,834 A * | 7/1997 | Harada | 437/210 |
| 5,691,215 A | 11/1997 | Dai et al. | 437/44 |
| 5,705,150 A * | 1/1998 | Sittler | 374/36 |
| 5,801,105 A * | 9/1998 | Yano | 438/785 |
| 6,013,573 A * | 1/2000 | Yagi | 438/619 |
| 6,276,205 B1 * | 8/2001 | McNie | 73/504.13 |
| 6,284,671 B1 * | 9/2001 | Schmuki | 438/745 |

FOREIGN PATENT DOCUMENTS

| | | | |
|---|---|---|---|
| CH | 665908 | 6/1988 | G01N/27/14 |
| DE | 3151891 | 7/1983 | G01N/27/12 |
| EP | 305963 | 3/1989 | G01N/31/10 |
| EP | 492700 | 7/1992 | G01N/27/414 |
| EP | 557642 | 9/1993 | G01N/33/02 |
| GB | 2127977 | 4/1984 | G01N/27/28 |
| WO | WO 96/09534 | 3/1996 | G01N/27/22 |
| WO | WO 00/75649 | 12/2000 | G01N/27/414 |

OTHER PUBLICATIONS

Natale et al, Multicomponent anakysis on polluted waters by means of an electronic tongue, Sensors and Actuators, B 44 (1997) pp. 423–428.

Legin et al, Tasting of Beverages using an electronic tongue, Sensors and Actuators, B 44 (1997) pps 291–296.

Schweizer–Berberich et al, Characterisation of food freshness with sensor arrays, Sensors and Actuators, B 18–19, (1994) pps 282–290.

* cited by examiner

*Primary Examiner*—John F. Niebling
*Assistant Examiner*—Andie C. Stevenson
(74) *Attorney, Agent, or Firm*—Hayes Soloway P.C.

(57) ABSTRACT

In order to obtain long time stability and usefulness for gas sensitive field-effect devices a micro structured surface is obtained below the final conducting layer. The conductive layer in the trenches or grooves will not only be protected to some extent but also they can constitute a conductive net with edges or boundaries that will remain essentially unchanged even if material is continuously lost along the borderline. The structure can be obtained in the layer laying directly below the conductive layer or in deeper lying layers with intermediate layers with even thickness.

25 Claims, 1 Drawing Sheet

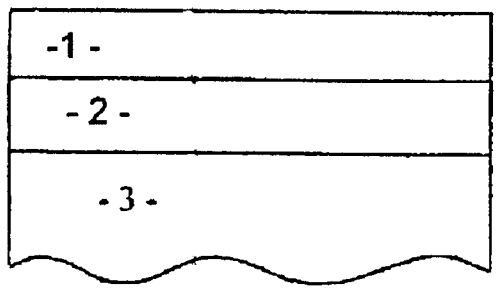
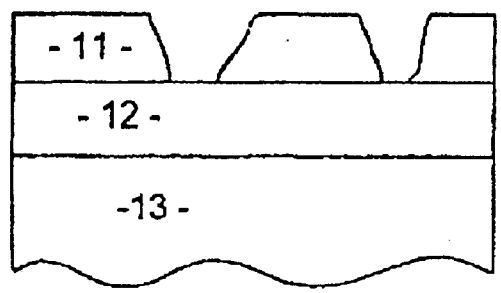
Fig. 1a  Fig. 1b
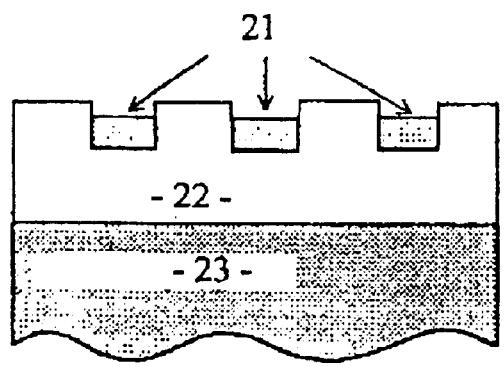
Fig. 2

DEVICE FOR GAS SENSING

TECHNICAL FIELD

The present invention relates to a device for gas sensing, particularly at high ambient temperatures, with improved long-term stability and reproducibility.

PRIOR ART

It is known that catalytic metals can be used as gates for gas sensitive field-effect devices (transistors, capacitors, diodes, etc). Thus they comprise metal-insulator-semiconductor or metal-semiconductor structures. Such devices may be used to measure small concentrations of molecules like hydrogen, hydrogen sulfide, alcohols, hydrocarbons, ammonia, amines, etc. The highest operation temperature is determined by the semiconductors used, which e.g. for silicon is about 250° C. but for silicon carbide about 1000° C.

The gas sensitivity occurs because reaction intermediaries, e.g. hydrogen atoms, give rise to electrical polarization phenomena at the metal-insulator or metal-semiconductor interface, which changes the electric field outside the semiconductor. FIGS. 1a and 1b show, in cross section, a schematic representation of two types of prior art catalytic field-effect sensors. More complex structures with additional buffer layers between the insulator and catalytic metal or between the semiconductor and metal have been fabricated in order to obtain an increased stability of the devices at elevated temperatures. FIG. 1a illustrates a device with a thick, continuous catalytic metal layer 1 on top of an insulator 1, in turn supported by a semiconductor, while FIG. 1b illustrates a device with a thin, porous catalytic layer of film 11 that leaves part of the underlying insulator 12 or semiconductor 13 surface exposed to the ambient gas molecules. Continuous catalytic film devices illustrated in FIG. 1a are only sensitive to hydrogen-containing molecules since only hydrogen atoms can diffuse through the metal and give rise to a dipole at the metal-insulator or metal-semi interface. Porous catalytic film devices illustrated in FIG. 1b, on the other hand, are sensitive to many more compounds since also reaction intermediaries located on the regions of the insulator or semiconductor exposed to the ambient can contribute to measurable electrical polarization effects. Therefore the porous catalytic film devices are more often used in chemical sensor arrays when there is a need to detect a broad range of molecules. The nature of the porous films, however, results in two important and well-known problems. First, it is difficult to have a reproducible production of this type of device since the sensitivity to different compounds to a large degree depends on the exact distribution of the catalytic metal across the surface. The sensitivity thus depends on the exact shape and distribution of the catalytic metal grains, parameters that are very difficult to control during the fabrication process. Secondly, the long-term stability of the devices is limited, especially at elevated temperatures, since the metal layer continuously undergoes a restructuring process, resulting in a time variation of the chemical sensitivity of the devices. In fact, for very thin catalytic metal films the thermodynamic equilibrium will only be reached when isolated metal islands have been formed resulting in a complete failure of the devices. There is thus a need for more reproducible and stable porous catalytic film field-effect sensors.

A SHORT DESCRIPTION OF THE INVENTION

The present invention discloses a gas sensitive porous catalytic film field-effect sensor offering improved reproducibility and long-term stability, especially at elevated operating temperatures. These improvements are obtained by depositing a thin catalytic layer 21 (FIG. 2) on an insulator 22 (supported by a semiconductor 23) or on a semiconductor that has a suitable and well-defined surface morphology. This morphology forces the catalytic film into a well-defined structure during the manufacturing process (thus improving the reproducibility) and prevents the metal from restructuring during operation (thus improving the long-term stability). An added advantage as compared to prior-art porous field-effect sensors is that the amount of catalytic material can be increased for a given amount of porosity. This will further improve the stability of the sensor devices since they will become less prone to poisoning effects. A typical device according to the invention is schematically illustrated in FIG. 2.

According to the first object of this invention, a field-effect gas sensor is fabricated by depositing a thin conducting layer onto a semiconducting substrate which has been given a suitable morphology by using masking, lithography, and etching techniques. The resulting device can, e.g., be operated as a Schottky-barrier device or as a tunneling device if a thin insulating layer has been added between the semiconductor and the conducting layer. The conducting layer can, e.g., consist of catalytic metals, alloys, or compounds or polymers in which case any semiconductor can be used. If a catalytically-active semiconducting substrate is used, the conducting layer could be catalytically active or inactive.

According to the second object of this invention, a field-effect gas sensor is fabricated by depositing a thin conducting layer onto a semiconducting substrate which has been given a suitable morphology by utilizing a naturally obtained morphology resulting from, e.g., an etching process or a deposition technique. The resulting device can, e.g., be operated as a Schottky-barrier device or as a tunneling device if a thin insulating layer has been added between the semiconductor and the conducting layer. The conducting layer can, e.g., consist of catalytic metals, alloys, or compounds or polymers in which case any semiconductor can be used. If a catalytically-active semiconducting substrate is used, the conducting layer could be catalytically active or inactive.

According to the third object of this invention, a field-effect gas sensor is fabricated by depositing a thin conducting layer onto an insulating layer grown on a semiconducting substrate which has been given a suitable morphology by using masking, lithography, and etching techniques. The resulting device can, e.g., be operated as a field-effect transistor or as a capacitor. The conducting layer can, e.g., consist of catalytic metals, alloys, or compounds or polymers in which case any insulator can be used. If a catalytically-active insulator is used, the conducting layer could be catalytically active or inactive.

According to the fourth object of this invention, a field-effect gas sensor is fabricated by depositing a thin conducting layer onto an insulating layer grown on a semiconducting substrate which has been given a suitable morphology by utilising a naturally obtained morphology resulting from, e.g., an etching process or a deposition technique. The resulting device can, e.g., be operated as a field-effect transistor or as a capacitor. The conducting layer can, e.g., consist of catalytic metals, alloys, or compounds or polymers in which case any insulator can be used. If a catalytically-active insulator is used, the conducting layer could be catalytically active or inactive.

According to the fifth object of this invention, a field-effect gas sensor is fabricated by depositing a thin conducting layer onto an insulating layer grown on a semiconducting substrate where the insulating layer has been given a suitable morphology by using masking, lithography, and etching techniques. The resulting device can, e.g., be operated as a field-effect transistor or as a capacitor. The conducting layer can, e.g., consist of catalytic metals, alloys, or compounds or polymers in which case any insulator can be used. If a catalytically-active insulator is used, the conducting layer could be catalytically active or inactive.

According to the sixth object of this invention, a field-effect gas sensor is fabricated by depositing a thin conducting layer onto an insulating layer grown on a semiconducting substrate where the insulating layer has been given a suitable morphology by utilising a naturally obtained morphology resulting from, e.g., an etching process or a deposition technique. The resulting device can, e.g., be operated as a field-effect transistor or as a capacitor. The conducting layer can, e.g., consist of catalytic metals, alloys, or compounds or polymers in which case any insulator can be used. If a catalytically-active insulator is used, the conducting layer could be catalytically active or inactive.

EXAMPLES OF DEVICES FABRICATED FOLLOWING THE OBJECTS OF THE INVENTION

Example 1

Above, it is mentioned that a semiconducting substrate or insulating layer with suitable morphology can be obtained using masking, lithography, and etching techniques. This process could, e.g., consist of the following steps. A resist is deposited onto the material that should be given a suitable morphology. The resist is patterned using e-beam lithography, e.g., by exposing a pattern of squares or circles of a suitable size, typically 100–10000 Å. After development of the resist, the unexposed resist is removed and the material below is etched to a suitable depth, typically 100–1000 Å. The resulting surface will consist of a regular array of 100–1000 Å high protrusions separated by trenches. The trenches will all be interconnected and the protrusions will be covered by resist.

(a) If the above described masking, lithography, and etching process is performed using a semiconducting substrate, a field-effect gas sensor according to the above described first object of the invention can be produced by depositing a thin conducting film (thickness typically 100–1000 Å) on top of the surface resulting from the above process leaving the protrusions covered by resist. After the deposition of the conducting film, the resist is dissolved using a suitable solvent such that the metal above the resist is removed. The resulting structure will consist of a semiconducting substrate with a grid of interconnected trenches almost filled with a conducting material. The resulting Schottky-barrier device (or tunneling device if a thin insulating layer has been added prior to the deposition of the conducting layer) will have a reproducible gas sensitivity since the structure and porosity of the conducting layer is defined by the trenches. Furthermore, the device will have a good long-term stability since the conducting layer is contained in the trenches and thus cannot restructure even upon high-temperature operation.

(b) If the above described masking, lithography, and etching process is performed using a semiconducting substrate, a field-effect gas sensor according to the above described first object of the invention can also be produced by depositing a thin conducting film (thickness typically 100–1000 Å) on top of the surface resulting from the above process after the resist covering the protrusions has been removed using a suitable solvent. In this case, the conducting film will cover the entire surface. The conducting material contained within the interconnected trenches will show the same stability and reproducibility as in the example 1(a) above. The conductive material on top of the protrusions will upon heating restructure by pulling away from the edges of the protrusions such that the contact with the conductive material within the trenches would be lost. This could lead to unwanted disturbances in the sensor response due to, e.g., charging effects. In order to eliminate such effects, it is possible to remove the conducting material on top of the protrusions, e.g., by sputtering at grazing incidence or by polishing.

(c) If the above described masking, lithography, and etching process is performed using a semiconducting substrate, a field-effect gas sensor according to the above described third object of the invention can be produced by growing a thin insulating layer on top of the surface resulting from the above process after the resist covering the protrusions has been removed using a suitable solvent. The insulator can either be grown using a deposition technique such as magnetron sputtering or by thermal growth of an oxide of the semiconducting substrate. The resulting structure will consist of an insulating layer with interconnected trenches. On top of this surface, a conducting layer can be deposited. The resulting field-effect transistor device or capacitor device will have a reproducible gas sensitivity since the structure and porosity of the conducting layer is defined by the trenches. Furthermore, the device will have a good long-term stability since the conducting layer is contained in the trenches and thus cannot restructure even upon high-temperature operation. As in the example (b) above, there will be conductive material on top of the protrusions that will restructure upon heating by pulling away from the edges of the protrusions, but this material can be removed using e.g. an extra sputtering or polishing step.

(d) If the above described masking, lithography, and etching process is performed using an insulating layer, a field-effect gas sensor according to the above described fifth object of the invention can be produced by growing a thin conductive layer on top of the surface resulting from the above process. The resist covering the protrusions can be removed prior to the deposition of the conductive layer using a suitable solvent. The resulting field-effect transistor device or capacitor device will have a reproducible gas sensitivity since the structure and porosity of the conducting layer is defined by the trenches. Furthermore, the device will have a good long-term stability since the conducting layer is contained in the trenches and thus cannot restructure even upon high-temperature operation. If the resist covering the protrusions has been removed prior to the deposition of the conductive layer there will be conductive material on top of the protrusions. As in the examples (b) and (c) above, this conductive material will restructure upon heating by pulling away from the edges of the protrusions, but this material can be removed using e.g. an extra sputtering or polishing step.

Example 2

Above, it is mentioned that a semiconducting substrate or insulating layer with suitable morphology can be obtained by utilising a naturally obtained morphology resulting from, e.g., an etching process or a deposition technique. Examples of etching techniques are the well-known (photo) electrochemical fabrication of porous layers of silicon and silicon carbide. The resulting layers do not have the extremely regular morphology as that which can be obtained using masking, lithography, and etching techniques, but the average morphology can be controlled to a high degree of accuracy. Although it is possible to prepare highly porous layers using (photo)electrochemical etching processes, it is sufficient for the purpose of this invention to prepare layers with a roughness on a scale of typically 100–1000 Å. Once these rough layers have been prepared, functioning field-effect gas sensor devices according to objects 2, 4, and 6 of this invention can be fabricated in analogy to the examples 1(a)–(d) above.

Example 3

Above, it is mentioned that a semiconducting substrate or insulating layer with suitable morphology can be obtained by utilising a naturally obtained morphology resulting from, e.g., an etching process or a deposition technique. An example of a deposition technique is the previously known deposition of cerium dioxide films. It has been shown that it is possible to grow cerium dioxide with preferentially exposed (111) surfaces in pyramidal protrusions on top amorphous silicon dioxide. The pyramidal protrusions typically have a lateral size of 100–800 Å and a height of 50–250 Å. Functioning field-effect gas sensor devices according to object 6 of this invention can be fabricated using these naturally microstructured cerium dioxide films in analogy to the example 1(d) above. This particular example is especially interesting in view of the known catalytic properties of cerium dioxide, which can be modified e.g. by adding trace amounts of copper such that a wide range of differently selective sensors can be made.

Example 4

A different example of a deposition technique which can be utilised in order to obtain a natural morphology suitable for fabrication of reproducible and stable field effect sensors is the well known deposition of nanoparticles. Several techniques exist by which particles of a reproducible size in the range 100–1000 Å can be deposited onto a substrate. Functioning field-effect gas sensor devices according to object 6 of this invention can be fabricated using such techniques in two ways. One way is by depositing insulating particles on top of an insulating layer after which a sensor is fabricated in analogy to the example 1(d) above. A second way is to deposit particles which can serve as an etch mask on top of the insulating layer such that the areas not covered by the particles can be etched resulting in an interconnected mesh of trenches. After removal of the particles using a second etch procedure, sensors can be fabricated by deposition of a thin conducting layer in analogy to the example 1(c) above. If, in a similar fashion, particles which can serve as an etch mask are deposited on top of a semiconducting substrate such that the areas not covered by the particles can be etched resulting in an interconnected mesh of trenches, sensors according to the second or forth object of this invention can be fabricated in analogy to the examples 1(b) and 1(c) above.

In the drawings FIG. 1a depicts a sensor with a continuous catalytic film or layer, FIG. 1b a sensor with a thin porous catalytic film and FIG. 2 a sensor device according to the invention with a structured insulator.

What is claimed is:

1. A method for the fabrication of a catalytic field-effect sensor which comprises patterning a substrate to form thereon a micro structured surface having a pattern of interconnected grooves or channels, and depositing a conductive layer over the micro structured surface.

2. A method according to claim 1, wherein the micro structured surface is formed on a semiconducting substrate.

3. A method according to claim 1, wherein the micro structured surface is formed on an insulating layer.

4. A method according to claim 1, wherein the micro structured surface is formed by masking, lithography or etching.

5. A method according to claim 1, wherein the micro structured surface is formed by deposition.

6. A method according to claim 5, wherein the deposition comprises sputtering.

7. A method according to claim 4, wherein the micro structured surface is formed by electrochemical or photo-electrochemical etching.

8. A method according to claim 1, wherein the micro structured surface is formed by fast drying or heating so that it cracks.

9. A method according to claim 1, and further including a step of heating the sensor so that the outer conductive layer is restructured to a stable configuration with essentially only conductive material in the trenches or channels in continuous contact over the sensor area.

10. A method according to claim 1, and further including a polishing step in which the conductive layer on protrusions or ridges of the micro structure is worked away.

11. A method according to claim 10, wherein said polishing is conducted by mechanical or sputter polishing at an oblique angle of incidence.

12. A method according to claim 4, wherein the micro structured surface is formed by anistropic etching.

13. A catalytic field-effect sensor having an outer conductive layer arranged on a micro structured surface, wherein the micro structured surface comprises a pattern of interconnected grooves or channels.

14. A sensor according to claim 13, wherein the outer conductive layer is polished away from the tops or protrusions of the micro structure so that the conductive layer has a pattern of an interconnected net of conductive material that is recessed into an underlying layer.

15. A method for the fabrication of a catalytic field-effect sensor comprising depositing a conductive layer over a micro structured surface on a substrate, and polishing the conductive layer to work conductive material from protrusions or ridges on the micro structured surface.

16. A method according to claim 15, wherein the micro structured surface is formed on a semiconducting substrate.

17. A method according to claim 15, wherein the micro structured surface is formed on an insulating layer.

18. A method according to claim 15, wherein the micro structured surface is formed by masking, lithography or etching.

19. A method according to claim 15, wherein the micro structured surface is formed by deposition.

20. A method according to claim 19, wherein the deposition comprises sputtering.

21. A method according to claim 15, wherein the micro structured surface is formed by electrochemical or photo-electrochemical etching.

22. A method according to claim 15, wherein the micro structured surface is formed by fast drying or heating so that it cracks.

23. A method according to claim 15, and further including a step of heating the sensor so that the outer conductive layer is restructured to a stable configuration with essentially only conductive material in trenches or channels in the structure in continuous contact over the sensor area.

24. A method according to claim 15, wherein said polishing is conducted by mechanical or sputter polishing at an oblique angle of incidence.

25. A method according to claim 19, wherein the micro structured surface is formed by anistropic etching.

* * * * *